(12) United States Patent
Cheng et al.

(10) Patent No.: US 11,651,672 B2
(45) Date of Patent: May 16, 2023

(54) SYSTEM AND METHOD FOR ALZHEIMER'S DISEASE RISK QUANTIFICATION UTILIZING INTERFEROMETRIC MICRO-DOPPLER RADAR AND ARTIFICIAL INTELLIGENCE

(71) Applicant: MS Technologies, Rockville, MD (US)

(72) Inventors: Shuchuan Jack Cheng, Potomac, MD (US); Yuan-Ming Fleming Lure, Potomac, MD (US)

(73) Assignee: MS TECHNOLOGIES, Rockville, MD (US)

( * ) Notice: Subject to any disclaimer, the term of this patent is extended or adjusted under 35 U.S.C. 154(b) by 0 days.

(21) Appl. No.: 17/992,722

(22) Filed: Nov. 22, 2022

(65) Prior Publication Data

US 2023/0078905 A1    Mar. 16, 2023

Related U.S. Application Data

(63) Continuation of application No. 17/970,330, filed on Oct. 20, 2022, which is a continuation-in-part of
(Continued)

(51) Int. Cl.
*G08B 21/00*    (2006.01)
*G08B 21/04*    (2006.01)
(Continued)

(52) U.S. Cl.
CPC .......... *G08B 21/043* (2013.01); *G01S 13/62* (2013.01); *G06N 20/00* (2019.01); *G08B 27/005* (2013.01)

(58) Field of Classification Search
CPC ..... G08B 21/043; G08B 27/005; G06N 20/00
See application file for complete search history.

(56) References Cited

U.S. PATENT DOCUMENTS 9,367,817 B2     6/2016  Schaffer et al.
10,817,070 B2   10/2020  Lien et al.
(Continued)

*Primary Examiner* — Ojiako K Nwugo
(74) *Attorney, Agent, or Firm* — Galvin Patent Law LLC; Brian R. Galvin

(57) ABSTRACT

A system and method for quantifying Alzheimer's disease (AD) risk using one or more interferometric micro-Doppler radars (IMDRs) and deep learning artificial intelligence to distinguish between cognitively unimpaired individuals and persons with AD based on gait analysis. The system utilizes IMDR to capture signals from both radial and transversal movement in three-dimensional space to further increase the accuracy for human gait estimation. New deep learning technologies are designed to complement traditional machine learning involving separate feature extraction followed-up with classification to process radar signature from different views including side, front, depth, limbs, and whole body where some motion patterns are not easily describable. The disclosed cross-talk deep model is the first to apply deep learning to learn IMDR signatures from two perpendicular directions jointly from both healthy and unhealthy individuals. Decision fusion is used to integrate classification results from feature-based classifier and deep learning AI to reach optimal decision.

20 Claims, 12 Drawing Sheets

Related U.S. Application Data application No. 17/866,021, filed on Jul. 15, 2022, which is a continuation-in-part of application No. 17/857,963, filed on Jul. 5, 2022, and a continuation-in-part of application No. 17/559,680, filed on Dec. 22, 2021, said application No. 17/857,963 is a continuation of application No. 17/116,686, filed on Dec. 9, 2020, now Pat. No. 11,380,181.

(60) Provisional application No. 63/230,946, filed on Aug. 9, 2021, provisional application No. 63/150,360, filed on Feb. 17, 2021, provisional application No. 63/150,335, filed on Feb. 17, 2021.

(51) Int. Cl.
  *G06N 20/00* (2019.01)
  *G08B 27/00* (2006.01)
  *G01S 13/62* (2006.01)

(56) References Cited

U.S. PATENT DOCUMENTS

| | | | |
|---|---|---|---|
| 2016/0147959 A1* | 5/2016 | Mariottini | G16H 50/20 706/46 |
| 2016/0278652 A1* | 9/2016 | Kaib | G16H 80/00 |
| 2019/0336085 A1* | 11/2019 | Kayser | A61B 5/447 |
| 2020/0013165 A1 | 1/2020 | Zhang et al. | |

* cited by examiner

SYSTEM AND METHOD FOR ALZHEIMER'S DISEASE RISK QUANTIFICATION UTILIZING INTERFEROMETRIC MICRO-DOPPLER RADAR AND ARTIFICIAL INTELLIGENCE

CROSS-REFERENCE TO RELATED APPLICATIONS

Priority is claimed in the application data sheet to the following patents or patent applications, the entire written description of each of which is expressly incorporated herein by reference in its entirety:
Ser. No. 63/230,946
Ser. No. 17/116,686
Ser. No. 17/970,330

BACKGROUND

Field of the Art

The disclosure relates to the field of radar systems, and more particularly to the field of interferometric micro-doppler radar systems for the detection of Alzheimer's disease risk.

Discussion of the State of the Art

More than five million people in the United States currently have Alzheimer's Disease (AD), and the number is expected to increase to 16 million by 2050. Neurobiological changes of AD occur decades before clinical symptoms arise. Thus, there is a growing consensus that treatment should target the disease in early phases, ideally before clinical symptoms manifest. Despite the high prevalence of AD, it is estimated that half of dementia cases remain undiagnosed. Researchers have found that, similar to gait abnormality in Parkinson disease (PD), gait impairments specific to AD exist. Therefore, the way older people walk may be a marker of severity of cognitive impairment or AD risk.

Existing devices to study human gait can be classified into two types: non-wearable sensors (NWS) and wearable sensors (WS). NWS (or ambient) systems require the use of controlled research facilities where the sensors are located to capture data on gait while the individual walks on a marked walkway. Some NWS include laser range scanners, infrared sensors, time-of-flight cameras, and floor sensor mats. WS systems analyze data and capture information about human gait during the person's everyday activities. WS systems use sensors located on several parts of the body, such as feet, knees, thigh or waist. Example WS systems include accelerometers, gyroscopic sensors, magnetometers, force sensors, extensometers, goniometers, active markers, electromyography, etc. Hybrid systems use a combination of both. There are several challenges related to NWS and WS: (1) NWS requires a specific set-up and can hardly be used in a daily living environment with floor mats being expensive and requiring patient compliance; (2) WS can be intrusive and may not be worn at all times (e.g., during bathing, due to forgetfulness, etc.) making them less effective.

Micro Doppler radar (MDR) technology has been investigated recently as an ambient sensor for human gait estimation that can overcome the above challenges of NWS and WS. MDR senses micro-motion-induced Doppler shifts and measures micro Doppler signatures (MDS)s in the joint time-frequency domain of human body parts (limbs, legs, arms, knees, joints, etc.) to estimate human motion speeds, directions, stride periods and sizes, and to characterize and discriminate human movement types. Recent studies have demonstrated the clear potential of MDR for gait estimation in healthy individuals and individuals with canes.

Lacking, however, is 1) a MDR system designed to effectively monitor gait among patients with AD or individuals at risk of AD, for 2) realistic human gait movements along different directions, and 3) a robust algorithm to estimate gaits from both algorithmically describable and indescribable salient gait patterns of AD patients. Another significant limitation of the conventional MDR for gait estimation is that only 1-dimensional body movement (i.e., in radial direction) can generate MDS from motion speeds, directions, stride periods and sizes. In other words, when an individual walks perpendicular to radial direction or gait involving body parts (limbs, legs, arms, knees, joints, etc.) 3-dimensional (3D) movement in transversal direction, the MDR will not capture such MDS and lose its accuracy.

What is needed is a system and method to facilitate the use of MDR as a pervasive indoor monitoring system, which utilizes an interferometric technology to extend existing MDR as "interferometric micro Doppler radar (IMDR)" system to estimate gait from 3D body movement for individuals.

SUMMARY

Accordingly, the inventor has conceived and reduced to practice, a system and method for quantifying Alzheimer's disease (AD) risk using one or more interferometric micro-Doppler radars (IMDRs) and deep learning artificial intelligence to distinguish between cognitively unimpaired individuals and persons with AD based on gait analysis. The system utilizes IMDR to capture signals from both radial and transversal movement in three-dimensional space to further increase the accuracy for human gait estimation. New deep learning technologies are designed to complement traditional machine learning involving separate feature extraction followed-up with classification to process radar signature from different views including side, front, depth, limbs, and whole body where some motion patterns are not easily describable. The disclosed cross-talk deep model is the first to apply deep learning to learn IMDR signatures from two perpendicular directions jointly from both healthy and unhealthy individuals. Decision fusion is used to integrate classification results from feature-based classifier and deep learning AI to reach optimal decision.

According to a preferred embodiment, a system for Alzheimer's disease risk quantification is disclosed, comprising: a computing device comprising a memory, a processor, and a non-volatile data storage device; and a radio-frequency module comprising electronic components that cause the radio-frequency module to: transmit an electromagnetic wave; receive a reflected electromagnetic wave; convert the reflected electromagnetic wave into a digital signal; and send the digital signal to a processor module; and a processor module comprising a first plurality of programming instructions stored in the memory of, and operating on the processor of, the computing device, wherein the first plurality of programming instructions, when operating on the processor, cause the computing device to: receive the digital signal; process the digital signal into a spectrogram; and process the spectrogram through one or more deep learning algorithms for predicting an Alzheimer's disease risk score, wherein the system for Alzheimer's disease risk quantification use one or more interferometric radio frequency modules whereby a radar gait signature is received into a combined spectrogram processed by one or more deep learning algorithms for predicting the Alzheimer's disease risk score.

According to another preferred embodiment, a method for Alzheimer's disease risk quantification is disclosed, comprising: transmitting an electromagnetic wave; receiving a reflected electromagnetic wave; converting the reflected electromagnetic wave into a digital signal; and sending the digital signal to a processor module; receiving the digital signal; processing the digital signal into a spectrogram; and processing the spectrogram through one or more deep learning algorithms for predicting an Alzheimer's disease risk score, wherein the system for Alzheimer's disease risk quantification use one or more interferometric radio frequency modules whereby a radar gait signature is received into a combined spectrogram processed by one or more deep learning algorithms for predicting the Alzheimer's disease risk score.

According to an aspect of an embodiment, the one or more deep learning algorithms is a long short-term memory neural network According to an aspect of an embodiment, two long short-term memory neural networks are developed in parallel.

According to an aspect of an embodiment, the two long short-term memory neural networks use cross-talk for connecting feature maps in the middle layers of each neural network.

According to an aspect of an embodiment, the radar gait signature comprises at least a radial movement and a transversal movement in three-dimensional space.

According to an aspect of an embodiment, the processor module is a software defined radio that can dynamically adapt to the available communication environment.

According to an aspect of an embodiment, the radar gait signature is generated from at least one of a side view, a front view, a depth view, a limbs view, and a whole body view.

According to an aspect of an embodiment, the processor module is further configured to: process the spectrogram through one or more machine learning algorithms for predicting a second Alzheimer's disease risk score; and integrate the Alzheimer's disease risk score and the second Alzheimer's disease risk score using decision fusion to determine an optimal risk score.

According to an aspect of an embodiment, the deep learning algorithms are trained on time-series data.

According to an aspect of an embodiment, a graphical user interface whereby a user may interact with the interferometric radio frequency module or processor module inputs, settings, and outputs.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

Figure 6:
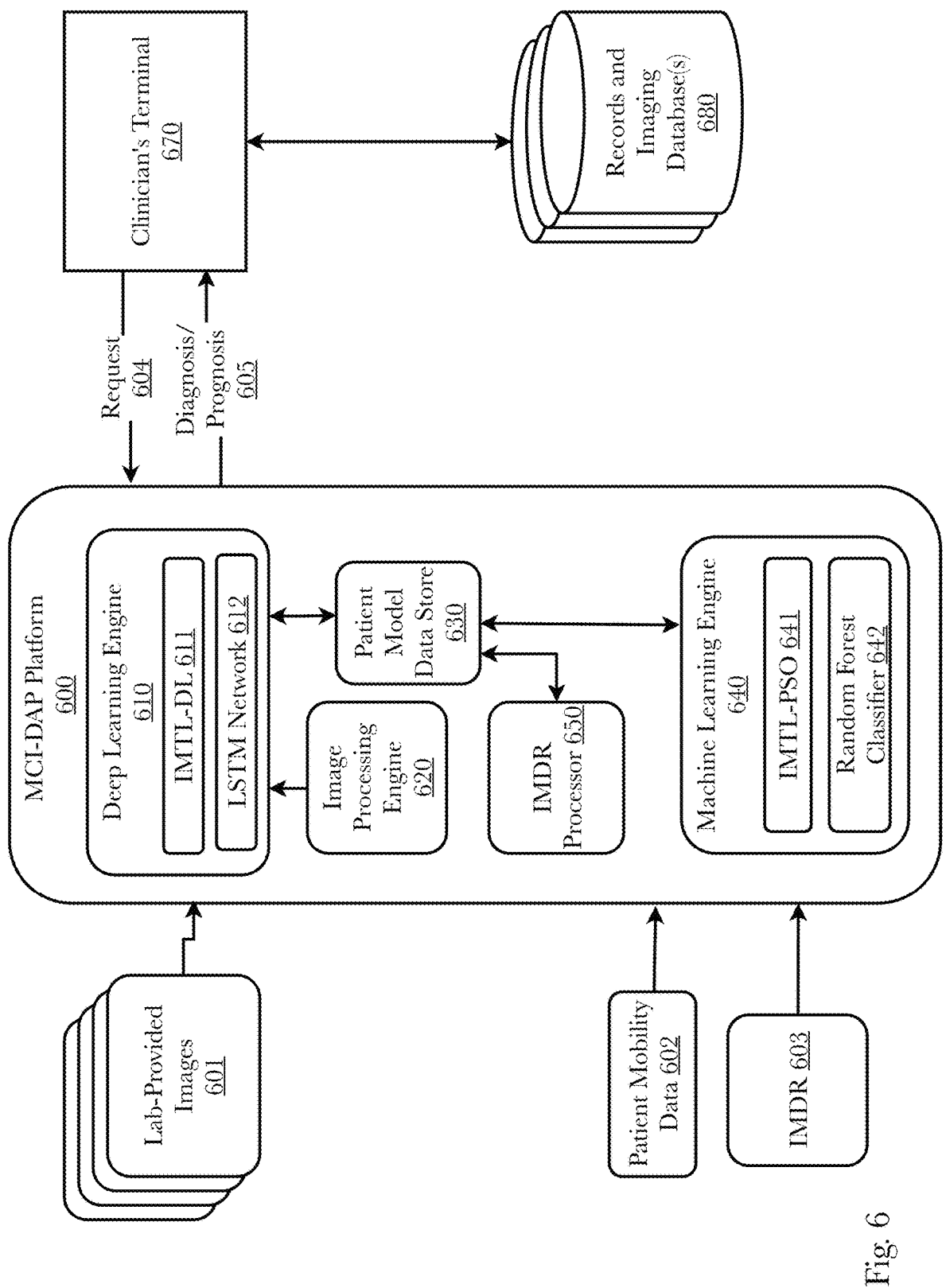
Figure 7:
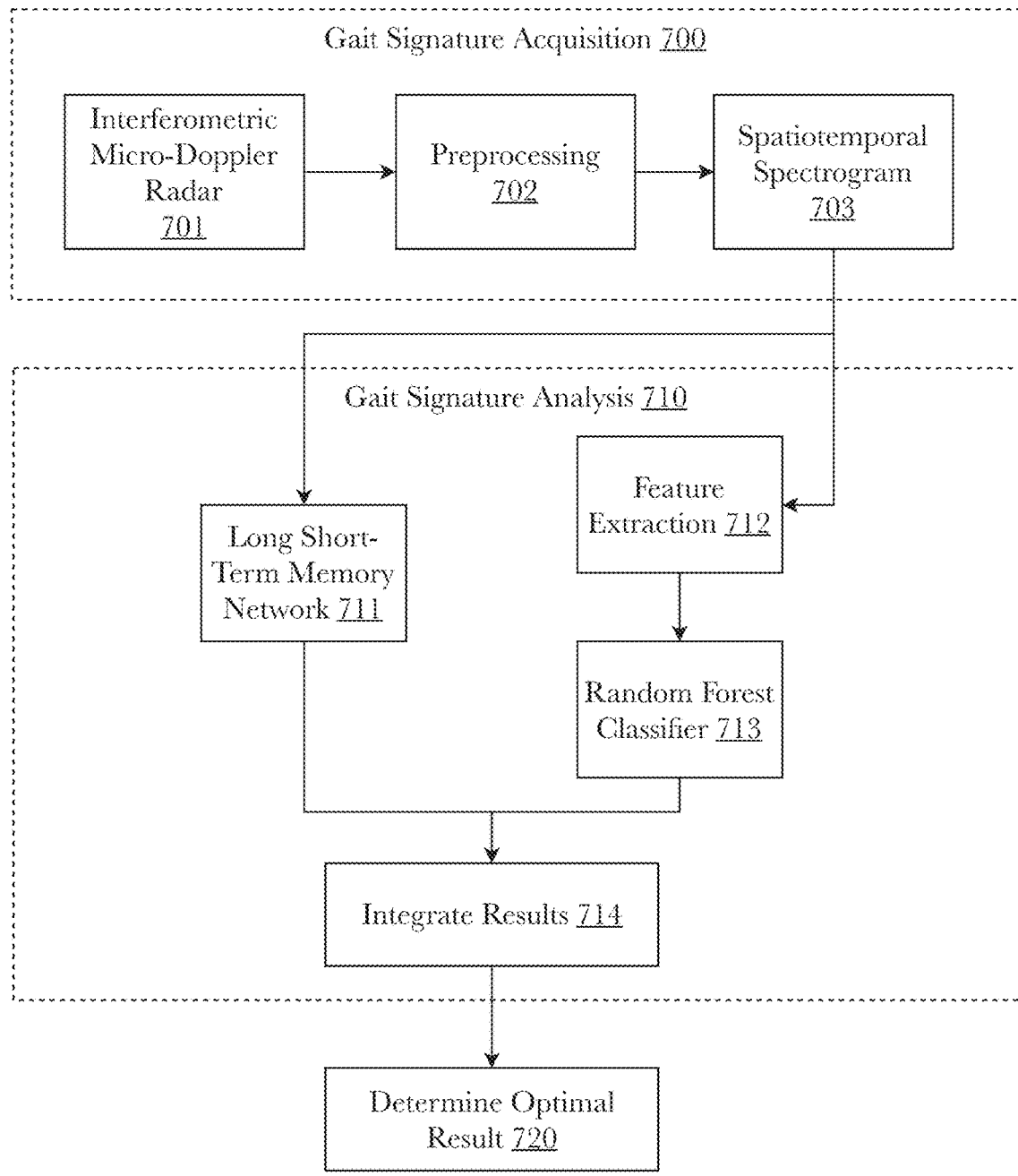

FIG. 6 is a block diagram illustrating an exemplary system architecture for a mild cognitive impairment—diagnostic and prognostic (MCI-DAP) platform configured to process gait feature data using various algorithms to support early diagnosis and prognosis of MCI and AD, according to an embodiment FIG. 7 is a flow diagram illustrating an exemplary method for a interferometric machine learning capable micro Doppler radar system, according to one aspect.

Figure 8:
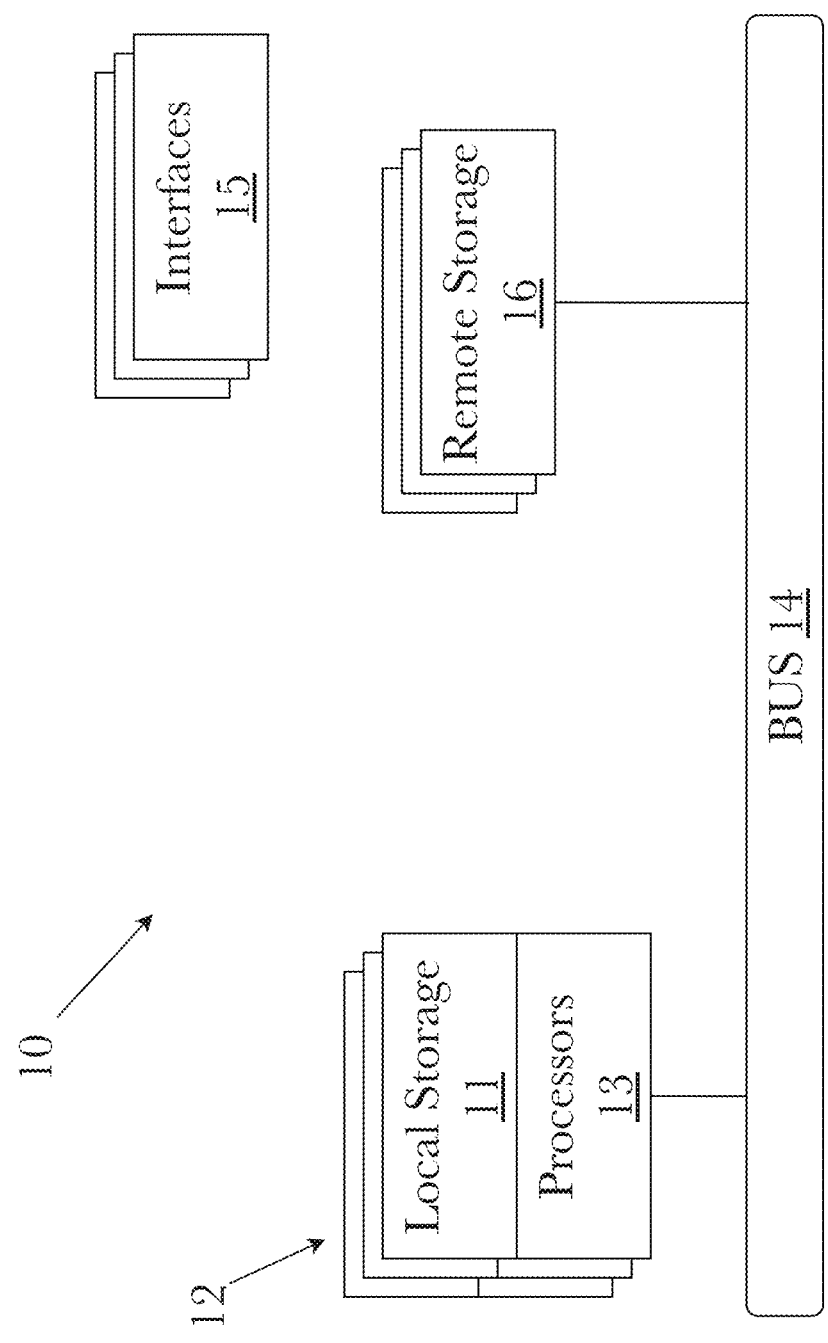

FIG. 8 is a block diagram illustrating an exemplary hardware architecture of a computing device.

Figure 9:
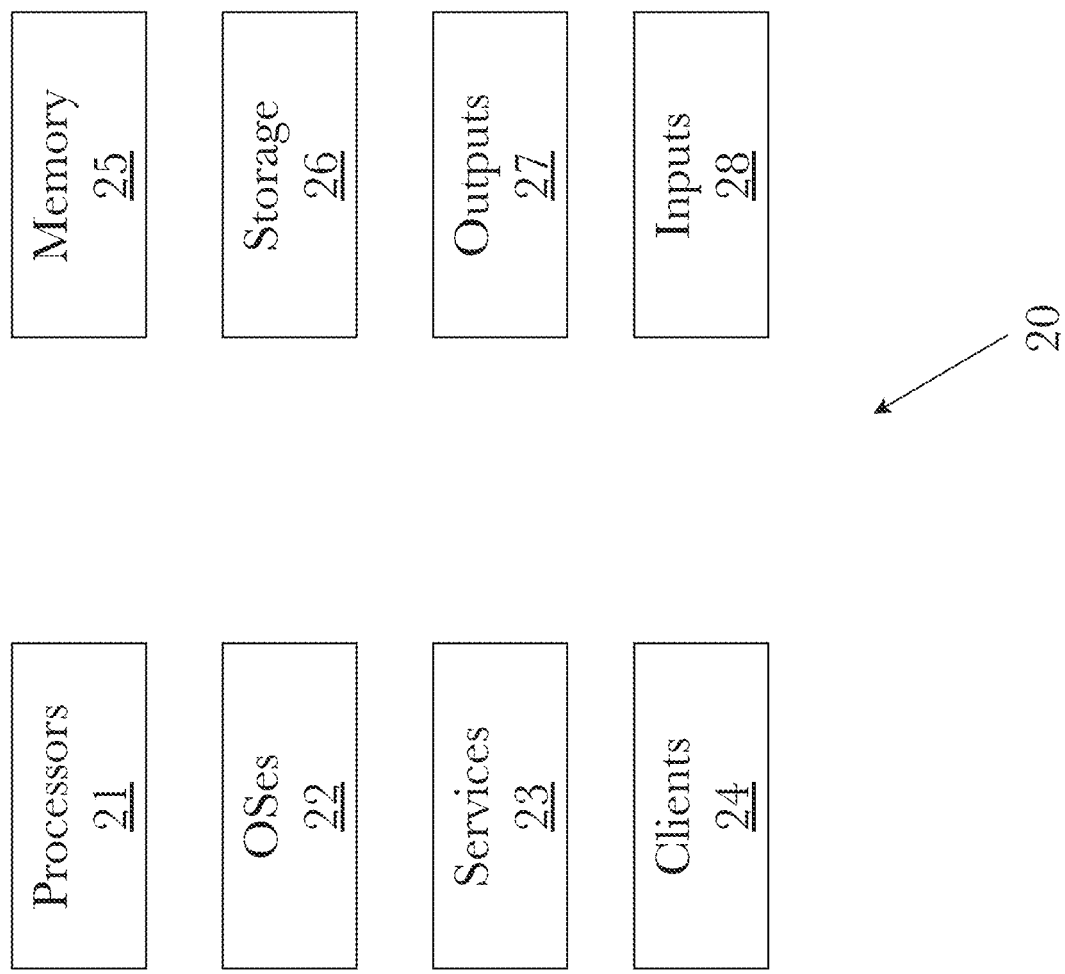

FIG. 9 is a block diagram illustrating an exemplary logical architecture for a client device.

Figure 10:
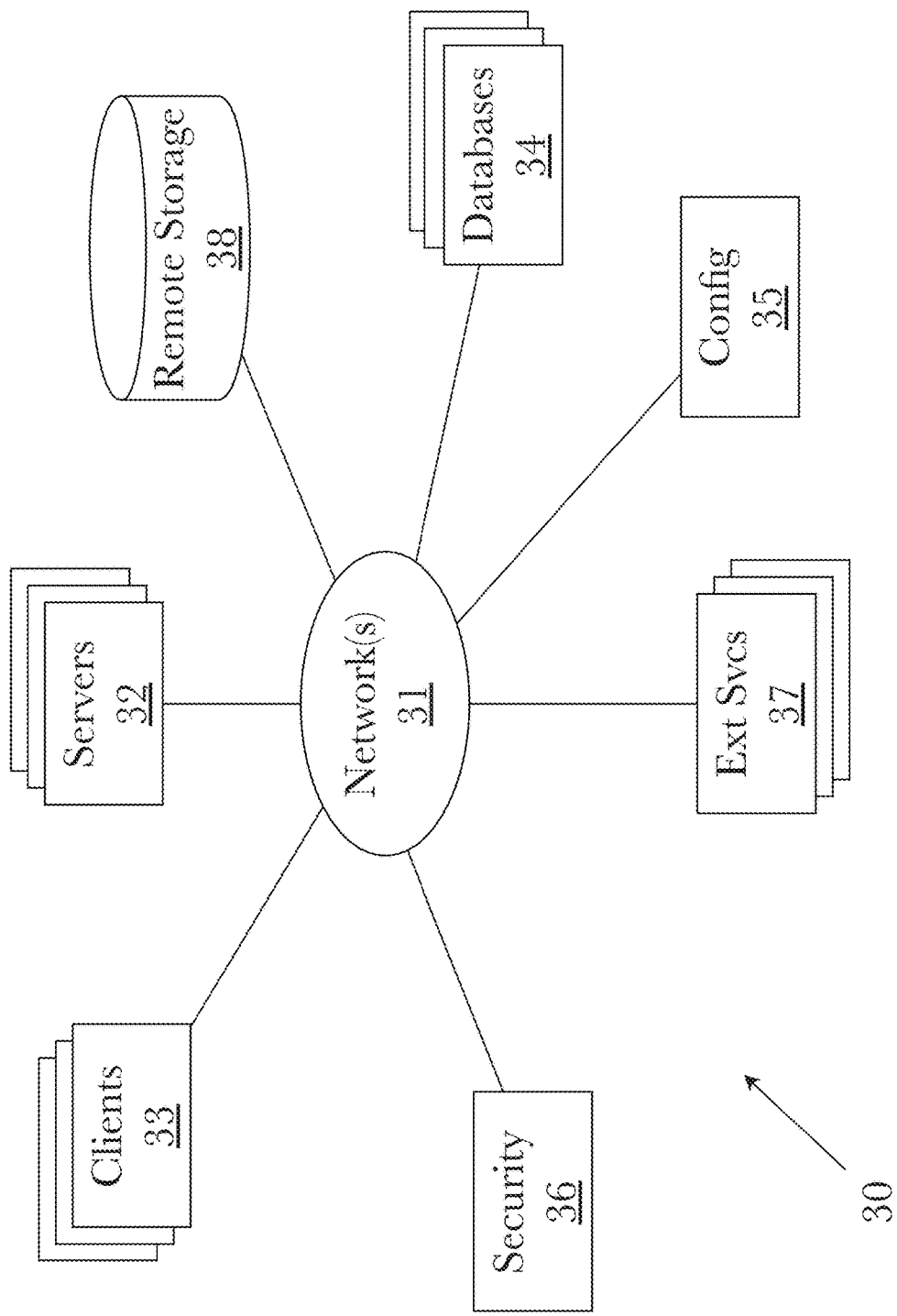

FIG. 10 is a block diagram showing an exemplary architectural arrangement of clients, servers, and external services.

Figure 11:
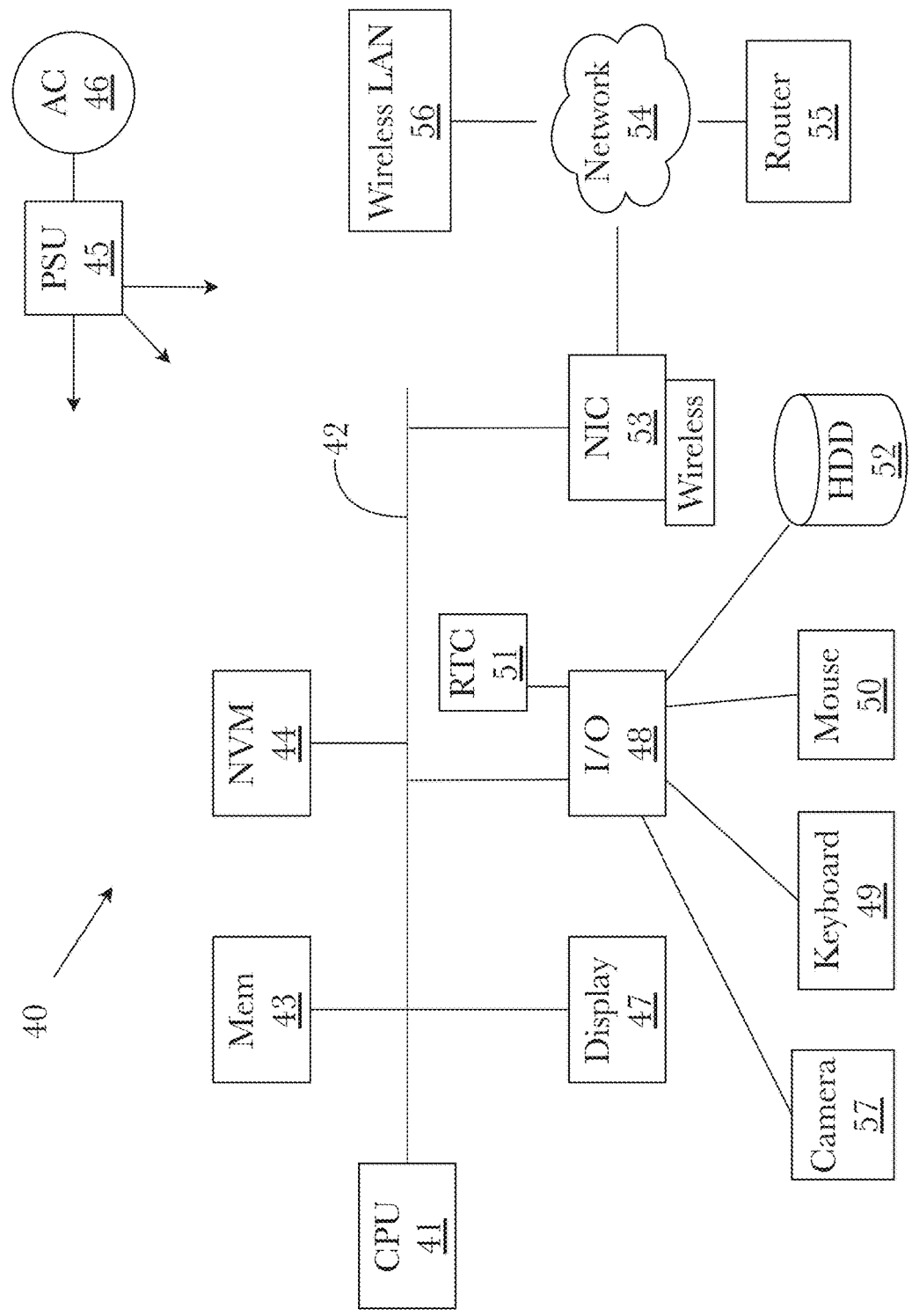

FIG. 11 is another block diagram illustrating an exemplary hardware architecture of a computing device.

DETAILED DESCRIPTION

Accordingly, the inventor has conceived and reduced to practice, a system and method for quantifying Alzheimer's disease (AD) risk using one or more interferometric micro-Doppler radars (IMDRs) and deep learning artificial intelligence to distinguish between cognitively unimpaired individuals and persons with AD based on gait analysis. The system utilizes IMDR to capture signals from both radial and transversal movement in three-dimensional space to further increase the accuracy for human gait estimation. New deep learning technologies are designed to complement traditional machine learning involving separate feature extraction followed-up with classification to process radar signature from different views including side, front, depth, limbs, and whole body where some motion patterns are not easily describable. The disclosed cross-talk deep model is the first to apply deep learning to learn IMDR signatures from two perpendicular directions jointly from both healthy and unhealthy individuals. Decision fusion is used to integrate classification results from feature-based classifier and deep learning AI to reach optimal decision.

The overarching aim of this application is to develop a safe pervasive compact device to be deployed in the living context (e.g., home, assisted living facility, nursing home) and clinical settings. Individuals can use the device for AD risk assessment to screen early-stage AD. The device can be built on software defined radio (SDR) technology such that the radar system can be compact, low-cost, and safe (safer than a cell phone). The system is easily translatable into a market product. The inventors have successfully developed a polarization MDR system to detect falls from older adults in indoor environment and will apply our successful experience to AD detection with sensitivity and specificity in this proposed research.

To facilitate the use of MDR as a pervasive indoor monitoring system, the inventors have developed an interferometric technology to extend their existing MDR as "interferometric micro Doppler radar (IMDR)' system to estimate gait from three-dimensional (3-D) body movement for individuals. Interferometer has been used in radio astronomy for the remote sensing of the earth. An interferometric radar receiver uses two separate receiver-channels with two antennas separated by a baseline for observing a far-field source. An object passing through the interferometric beam pattern will produce an oscillation whose frequency is directly proportional to the angular velocity of the object therefore the transversal signature represented in 3-D space will be captured to significantly improve the accuracy.

The system can be built on interferometric technology to benefit from one transmitter channel and two receiver channels to capture multi-dimensional body movements for individual. Additionally, the system and method employ feature-driven classification and data-driven deep learning to constantly monitor individuals' daily activities to capture gait and body movement which in turn may be associated with the risk of AD. The technology can also be easily deployed as hand-held device to analyze the gait of adults. Since micro Doppler signatures (MDS) are not visible to human eyes to identify any shape of a body part, the privacy of individually can be fully protected The disclosed IMDR system will generate a spatiotemporal gait features (STGF) represented in a joint time-frequency domain that provides information in the time (temporal) domain to exploit time-varying spatial velocity characteristics of the locomotion of human body segments of the swinging arms and legs of a normal person walking.

The inventors have conducted gait experiments for the collection of STGF from cognitively unimpaired and AD individuals. Both single-task and dual-tasks tests were performed to generate STGF for subsequent development and assessment of a new gait estimation algorithm.

The architecture for distinguishing between cognitively unimpaired and persons with AD, and for estimating AD risk in the long-term, consists of gait feature extraction, random forest classification, long short-term memory (LSTM) deep learning AI and decision fusion. A traditional feature extraction followed up with classification will be applied to well-known radar gait signature as well as deep learning AI to mine unknown indescribable salient properties. The IMDR gait signatures generated will be fed into this assessment system. The output of this system will be assessed risk score indicating the risk for AD.

Additionally, existing research including research conducted by the inventors has explored algorithmically describable features (e.g., velocity, cadence, step length, width, etc. for feet) to estimate gait for healthy individuals using traditional machine learning that involves a 2-steps process of (1) extracting features (for algorithmically describable features); and (2) feeding selected features into classification and prediction models (e.g., support vector machine, random forest classification, etc.). However, gait and body movement from early-stage AD patients possess subtle and indescribable salient characteristics and features which traditional feature extraction may not identify appropriately to reach desirable accuracy. To overcome this issue, deep learning artificial intelligence (AI) which integrates feature extraction and classification as an end-to-end network has taken place with considerable improvements on detectability comparing to the conventional 2-step machine learning methods. The inventors have successfully developed new deep learning AI techniques for the prognosis and diagnosis of AD using neuroimaging such as MRI, PET; and fall detection using radar data in a separate effort. The inventors have also developed decision fusion (like ensemble approach) to join different and complementary classification methods for optimal decisions. The disclosed system and methods build upon this previous work and develop new deep learning models as an integral part of IMDR to improve the robustness and accuracy of the gait estimation to distinguish between cognitively unimpaired and persons with AD, and potentially to also estimate AD risk in the long-term.

The successfully developed IMDR technology can be a passive, lightweight, affordable, compact, radiation frequency (RF) safe, and low-power device to constantly monitor individuals' daily activities and to detect gait changes which in turn may be associated with the risk of AD. The technology can also be easily deployed as hand-held device to analyze the gait of adults. Since MDS are not visible to human eyes to identify any shape of body part, the privacy of individually can be fully protected. The IMDR can be a cost-effective (~$100-$200) home product to monitor an adult continuously in a private, non-intrusive fashion, and seamlessly send an alert (e.g., via cellphone or Wi-Fi) to family members, caregivers, and/or healthcare professionals when an abnormality is detected.

The US market for AD healthcare is expected to exceed $200 billion each year. The technology can be used in various indoor environments and will track a person's everyday activities to estimate risk of AD in the long-term. The system may serve as either an early-stage AD screening system or as a supplementary system to existing diagnostic tools in the future. Furthermore, the disclosed system could work with clinical and industry partners to increase the quality of care of older adults, increase the accuracy, household-friendliness and clinical-friendliness, and to assist in the treatment, prevention, de-acceleration of AD for large-scale testing to receive regulatory clearance of the product.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

"MCI" or "mild cognitive impairment" as used herein means a neurocognitive disorder which involves cognitive impairments beyond those expected based on an individual's age and education, but which are not significant enough to interfere with instrumental activities of daily living. MCI may occur as a transitional stage between normal aging and dementia, especially Alzheimer's disease.

Conceptual Architecture

Figure 1:
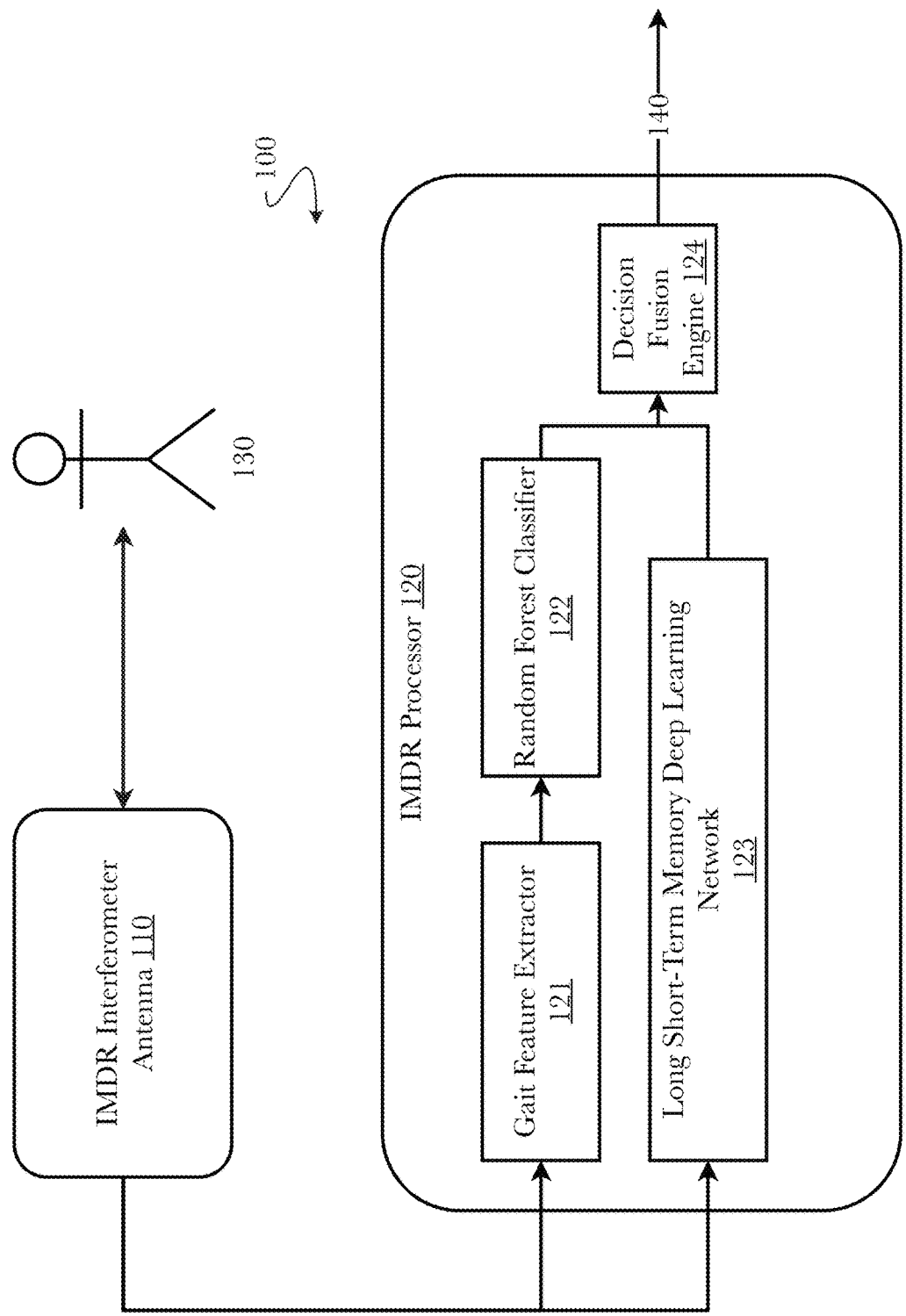
FIG. 1 is a block diagram illustrating an exemplary system architecture for a deep learning capable interferometric micro Doppler radar system comprising at least two components: the interferometric Tx/Rx antenna to capture radar gait signature; and IMDR processor to assess AD risk, according to one aspect.

FIG. 1 is a block diagram illustrating an exemplary system architecture for a deep learning capable interferometric micro Doppler radar system 100 comprising at least two components: the interferometric Tx/Rx antenna 110 designed to capture a radar gait signature of an individual 130 (e.g., medical patient, etc.); and IMDR processor 120 configured to assess AD risk, according to one aspect. The overall architecture for IMDR for assessment of AD risk may comprise an interferometric Tx/Rx antenna to capture radar gait signature and IMDR processor to assess AD risk. During Phase I period, we will develop and configure prototype IMDR system to conduct gait experiments to generate radar signature to develop AI algorithm for the assessment of AD risk. According to various embodiments, system 100 is configured to conduct gait measurements/experiments to generate radar signatures to develop one or more AI algorithms for the assessment of AD risk. During operation, system 100 may receive radar gait data associated with an individual (e.g., clinical patient), extract features from the radar gait data, and process the extracted features through one or more trained machine and deep learning models to produce as output, a predicted AD risk score 140 for the individual.

According to an embodiment, IMDR processor 120 may comprise various modules, gait feature extractor 121, random forest predictor 122, a long short-term memory (LSTM) deep learning network 123, and a decision fusion engine 124, each configured to process received radar data from IMDR interferometer antenna 110 in order to generate as output an Alzheimer's Disease risk score 140 (e.g., a prediction of AD risk or no AD risk, a probability, etc.) which can be applied to diagnosis and prognosis of AD and/or mild cognitive impairment (MCI). Together, these modules represent the machine and deep learning aspects of system 100. To train the underlying learning algorithms that support the predictive capabilities of system 100, gait training data may be acquired for both individuals with AD and cognitively unimpaired individuals and generation of corresponding human gait signatures from IMDR antenna 110 may be also be used as training data. In further training tasks, a more stratified sample of AD patients including early-stage AD patients and primarily MCI patients can be used. Patients with moderate to severe AD that meet the NIA-AA criteria for AD and score less than or equal to twenty on Min-Mental State Examination (MMSE) and controls (equal number of men and women) with similar ages and no sign of cognitive impairment (e.g., score greater than or equal to twenty-four on MMSE, functional independence, no diagnosis of dementia, no diagnosis of PD, and not on treatment for dementia or PD medication, etc.) may be selected for model training tasks.

During model training, all participants with AD will be able to walk for two minutes without using a walker (cane is acceptable). During this two minute time period, participants will be monitored by IMDR antenna 110 which produces measurements related to the participants gait and body movements. Training data collection may be conducted in an environment equipped with a walkway and safety device (to prevent any accident). The system 100 extracts gait patterns from all participants. According to various embodiments, two types of gait assessments can be conducted: single-task and dual-task walking of ten meters. Single-task test: participants will be asked to walk on the walkway at their usual pace in a quiet, will-lit room wearing comfortable footwear without the use of any mobility aids. Dual-task test: participants will walk a their usual pace on the walkway while performing the following cognitive tasks aloud: walk towards the IMDR antenna 110 and across the IMDR antenna slowly and with/without arm swinging toward and away relative to the IMDR antenna's line of sight, between approximately 4.5 meters and one meter from the antenna feed point. Each group (AD and healthy participants) will have at least 1,400 gait image patterns (e.g., 6 patients×3 dual-tasks×2 directions×2 arm-swing×20 walks) which can be used to train the learning algorithms comprising IMDR processor 120.

According to various embodiments, the architecture for distinguishing between cognitively unimpaired and persons with AD, and for estimating AD risk in the long-term, comprises gait feature extractor 121, random forest classifier 122, long short-term memory deep learning AI 123, and decision fusion engine 124. A traditional feature extraction process followed up with classification can be applied to well-known radar gait signatures as well as deep learning artificial intelligence to mine unknown, indescribable salient properties related to AD and/or MCI. The IMDR gait signatures generated above can be fed into IMDR processor 120 to output an assessed risk score indicating the risk of AD for an individual.

Human gait features can include, but are not limited to, velocity, number of steps per time unit (i.e., cadence), step length, stride length, step width, step angle step time, swing time for each foot, support time, duration of the stops, existence of tremors when walking, angles of the different joints, and body posture. MDSs of human gait have been investigated since the late 1990s by various parties. The MDS pattern of normal walking is a mono pattern (in 2D space) whereas abnormal walking may sway back and rock and, thus, appearing in a stereo 3D space which will only be captured by IMDR antenna 110. The 3D MDSs are represented in a joint time-frequency domain that provides additional information in the time domain to exploit time-varying Doppler characteristics (spatiotemporal spectrogram (STGF)) of the locomotion of human body and cadence-velocity diagram (CVD), where velocity is proportional to the observed Doppler shifts. According to an embodiment, gait feature extractor 121 will extract physical features and subspace features sets on both STGF and CVD signature space. Physical features have been widely used for radar-based human activity recognition including: torso Doppler frequency, total Doppler bandwidth, offset of the total Doppler, Doppler bandwidth without micro-Doppler effects, period of the limb motion or stride rate, average radial velocity, stride length, radar cross-section of some moving body components (e.g., gait amplitude ratio), gait periodicity (corresponding to stride rate), maximal Doppler shift, etc. According to an embodiment, in subspace, principal component analysis may be applied for the intrinsic features of the walking styles bearing multiple correspondence to human motion kinematics using singular value decomposition to decompose the data matrix.

According to various embodiments, a random forest classification model is developed leveraging a similar model that has successfully been used for the estimation of fall risk (for a more detailed description of the fall risk model, please refer to U.S. patent application Ser. No. 17/116,686 the entirety of which is included herein by reference). A random forest is a well-studied supervised machine learning algorithm, and it is applied to system 100 to classify radar gait features. Random forest classifier 122 creates a forest with a number of trees, with more trees in the forest it is more likely to provide robust predictions with high accuracy. Each decision tree is created from randomly chosen features (i.e., radar gait features) from participants and utilizing sets of rules to predict AD risk. Finally, votes are calculated for each predicted output from the decision trees, and majority voting is considered to select the final prediction. This method has the advantages to handle missing data values and provide robust predictions without overfitting.

Since gaits involve a sequential movement, long short-term memory networks 123 may be developed for classifying, processing, and making assessments based on time series data. An LSTM 123 cell is capable of learning long-term dependencies from those indescribable salient properties which is a variation of a recurrent neural network. A similar LSTM network has been successfully developed for fall detection applications, and such a network may be leveraged and applied to the one or more LSTM networks 123 in order to make AD risk predictions based on radar gait data. For a more detailed description of the LSTM fall risk model, please refer to U.S. patent application Ser. No. 17/116,686 the entirety of which is included herein by reference. According to various embodiments, this previously developed LSTM and deep learning models will serve as the basis for transfer learning to mitigate the potential limitation of training samples. Specifically, recognizing the innovation of the interferometric radar technology (IMDR antenna 110 and IMDR processor 120) will generate signatures from two perpendicular directions (e.g., radial and transverse movements), two LSTM models may be developed in parallel, and cross talk (i.e., connecting feature maps in the middle layers) will be established to fully take advantage of complementary information from the two channels.

Decision fusion engine 124 may receive and combine the results from different classifiers (e.g., random forest classifier 122 and LSTM network 123) to generate the optimal classification. According to various embodiments, decision fusion is a Bayesian classification problem that compares a likelihood ratio (e.g., between conditional probability of true classification vs. miss classification) with a minimum probability of classification error. An optimal decision fusion rule (e.g. Chair-Varshney fusion rule) will be used with implementation of a modified back-propagation (BP) neural network training procedure: 1) create receiver operating characteristic curves (ROCs) for each classifier or confusion matrix, including probabilities of true positives, false alarm, and false detection for individual classifier; 2) design a multiple layer neural network such that its connections are initiated based on the Bayesian conditions; and 3) present the input and desired output to the network and apply BP training to update the weights.

According to some embodiments, for model training and validation purposes a "divide-and-conquer' strategy may be used in conjunction with supervised BP training mechanism(s) to train each module (e.g., random forest classifier 122 and LSTM network 123) individually. Among collected radar signature images, a stratified 10-fold cross validation may be applied to repetitively train and validate modules 122, 123; though the stratified cross validation method generally performs well, different embodiments may use alternate resampling approaches (e.g., bootstrap) to minimize the variance and bias of performance outcomes. The performance of the trained modules can be examined using common performance metrics such as ROC curves, area and ROC curves (AUC), sensitivity, specificity, and F1 score. If a model/module does not reach a satisfactory level of performance, the design of the modules may be adjusted in aspects such as resizing the input image, adjusting the structures (e.g., increase/decrease the number of layers), use other base structure, and a different basis for transfer learning. In some aspects, techniques such as GradCAM and SHAP gradient explainers may be used to enhance the interpretability of the machine and deep learning algorithms supporting modules 122, 123.

The disclosed IMDR system 100 can provide a variety of advantages over other types of systems. For example, the range information may be obtained by simply measuring the difference between the transmitted and received frequencies via the simple FFT, simultaneous measurement of range and relative velocity is possible, low transmit power can still achieve high processing gain by use of large product of sweep-time and bandwidth, and the baseband signal falls in low frequency band and, thus, simplifies the realization of processing circuits.

In an embodiment, IMDR system 100 is configured to process both continuous wave and frequency modulated continuous wave signals according to the following specifications: setting a center frequency at 24.125 GHz; setting the bandwidth to 250 MHz; setting a sweep time between 0.25 ms and 5.0 ms; setting the number of samples per sweep to between 64-1024 samples; setting maximal transmit power to 0.05 W; setting the noise figure to 10 dB; and setting the maximum detectable range to 20 m at SNR: 13 dB and RCS: 1.0 sm.

Figure 2:
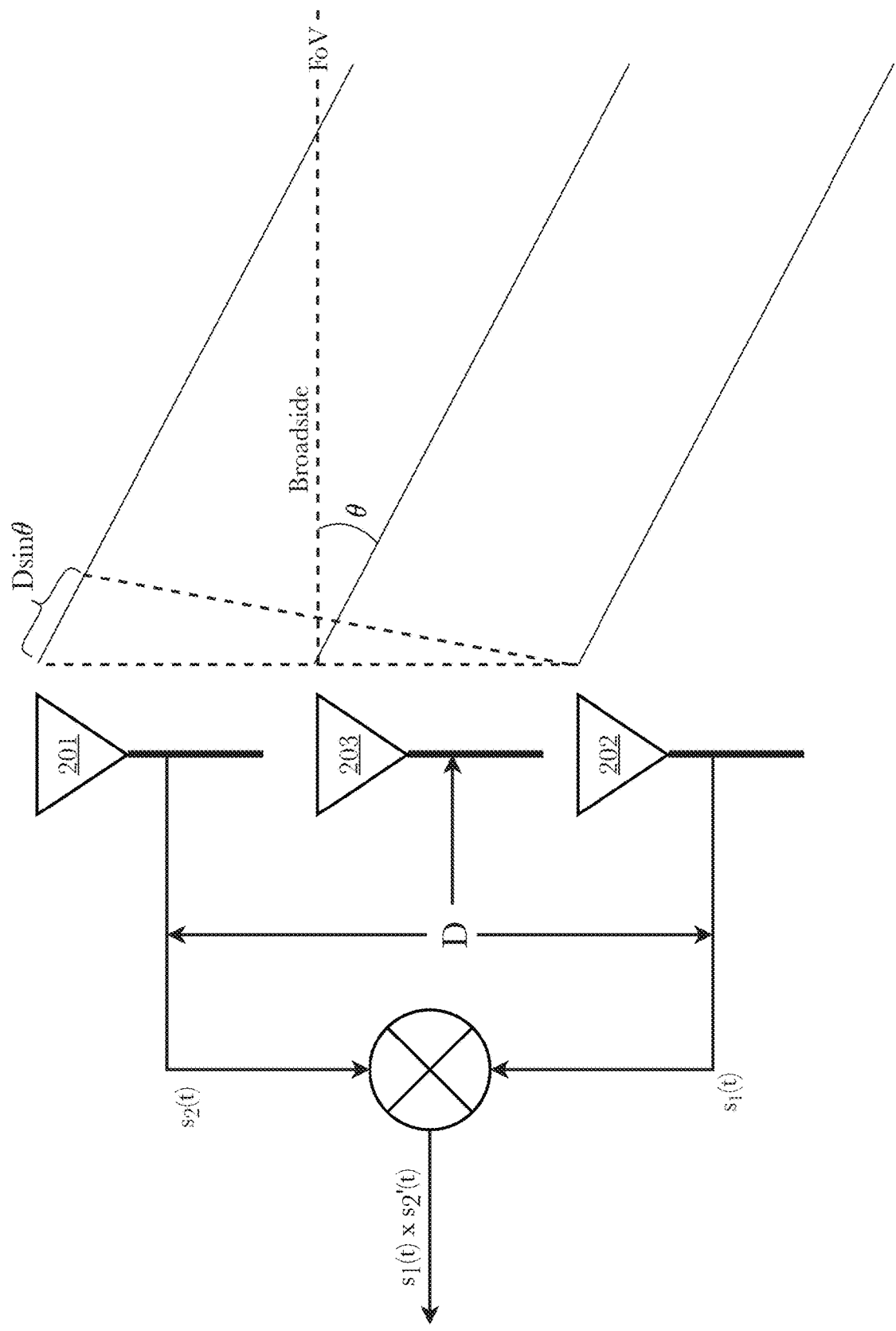
FIG. 2 is a block diagram illustrating an exemplary architecture for two-channel interferometric correlator receiver observing a source, according to one aspect.

FIG. 2 is a block diagram illustrating an exemplary architecture for two-channel interferometric correlator receiver observing a source, according to one aspect. The proposed interferometric radar is based on the principle of Michelson interferometry. According to various embodiments, the configuration of a two-channel interferometric correlator receiver system will be used comprising at least two receivers 201, 203 and a transmitter 202. For near broadside of field of view (FoV), the interferometric frequency shift is proportional to the angular velocity and space (D) between the two receiving antennas. The conventional Doppler frequency shift is proportional to the radial velocity. Thus, by combining the traditional Doppler measurement of radial velocity with the angular velocity measured by the interferometric receiver, the true 2-D velocity can be measured. The angular velocity measured through interferometric frequency shift is a good complementary feature to the radial velocity measured. Because an abnormal gaiting may sway and rock, thus, a stereo interferometric radar is better than a mono radar for capturing these abnormal gait features.

Figure 3:
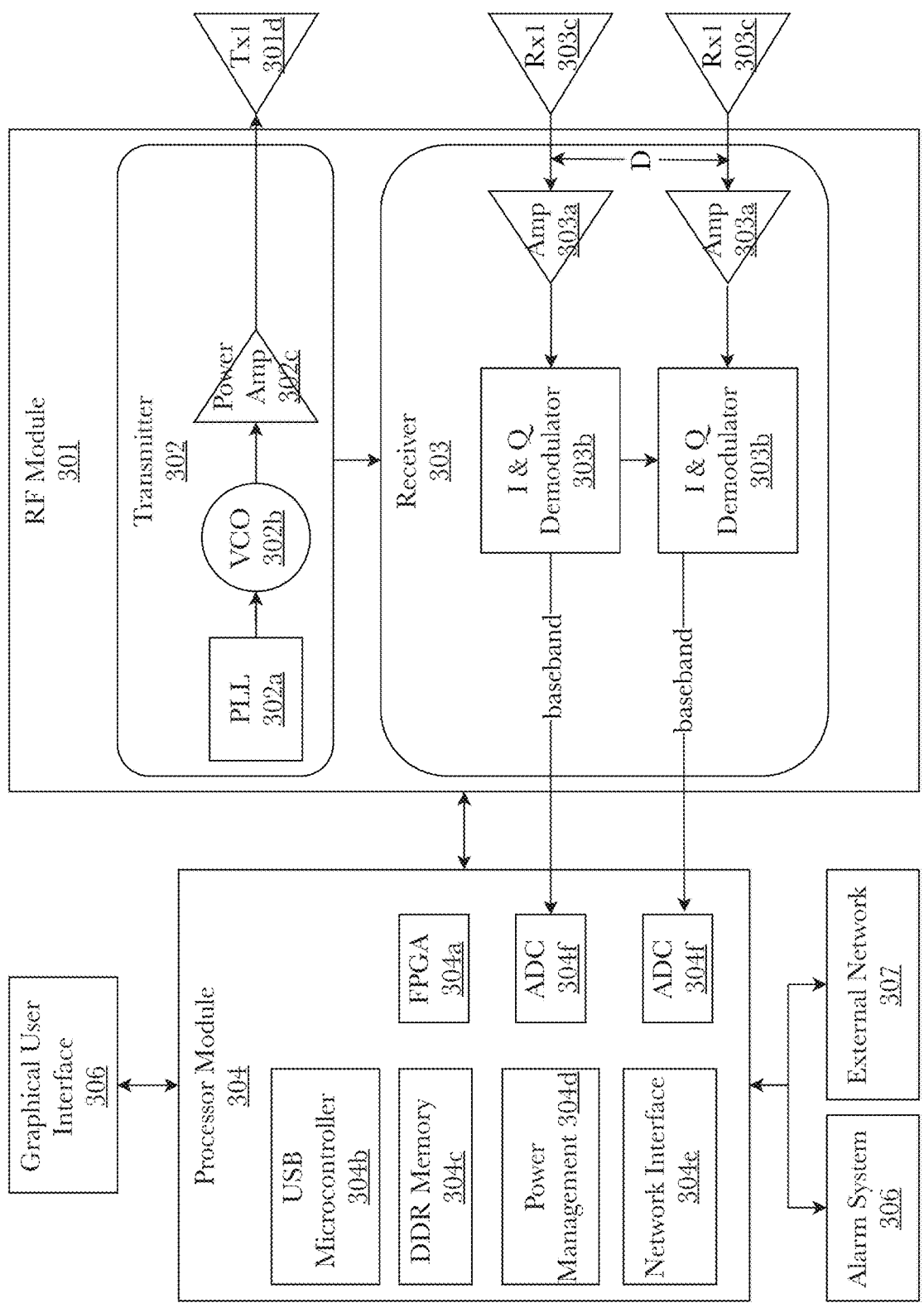
FIG. 3 is a block diagram illustrating an exemplary system architecture for an interferometric micro-doppler radar, according to an aspect.

FIG. 3 is a block diagram illustrating an exemplary system architecture for an interferometric machine learning capable micro-doppler radar system, according to an aspect. According to a preferred embodiment, a interferometric MDR (IMDR) system comprises a radio-frequency (RF) module 301 and a processor module 304 such that range and gait information may be obtained by measuring a beat frequency via Fast Fourier Transforms (FFT). In one such embodiment, an RF module 301 additionally uses a transmitter 302 that employs a phase-locked-loop (PLL) 302a to lock a RF output frequency to a phase of a stable reference oscillator 302b. Transmitter 302 also uses a power amplifier 302c to at least one transmitter channel 301d.

Received radio waves may be processed through a low noise amplifier 303a before being passed to a quadrature phase demodulator 303b which is used to avoid the self-image effect. Furthermore, a received complex signal may be directly mixed with a complex local oscillator from voltage-controlled oscillator 302b such that only one sideband of a received complex signal may be converted to a baseband frequency region. A series of analog-to-digital convertors 304c may convert radio waves from analog to digital before forwarding the now-digital radio signal to a processor module 304. The proposed architecture of the IMDR, shown in FIG. 3, can use a homodyne or zero-intermediate frequency (zero-IF) architecture. In the RF module 301, the receiver 303 may be a direct conversion (homodyne) receiver. The radar may have at least one transmitter channel 301d and at least two receiver channels 303c. The radar output is complex I & Q data that are used to do correlation process and exploit radial and transposal velocity characterization.

According to a preferred embodiment, processor module 304 may use an FPGA (field-programmable gate array) 304a as a microcontroller and microprocessor. Other microcontrollers and microprocessors known in the art may be substituted as desired. Typical components of a processor module 304 include USB microcontrollers 304b, DDR memory 304c or other memory modules, power management systems 304d, and network interfaces 304e such as ethernet or Wi-Fi. According to a preferred embodiment, a processor module 304 may act as a SDR (software-defined radio) offering compactness and flexibility by supporting operation mode, waveform, bandwidth, and processing functions through software protocols. An SDR may provide various abilities to integrate various software-defined functions for range and Doppler (velocity) measurements and sensing of micro-motions.

Other aspects include a use of highly integrated systems-on-chip (SoC) in both RF module 301 and processor module 304. This contributes to an overall form factor in order to achieve compactness, lightweight, and low power consumption. A graphical user interface (GUI) 306 may be used to select various options on signal waveforms, operating parameters, filtering types, and lengths of data recording; doing so may enable rapid data collection during gait observation experiments and for a subsequent development of gait based AD prediction or detection classification algorithms. A GUI may clearly display baseband signals in the time, frequency, and combined time-frequency domains in real time, and display micro-Doppler and polarization signatures.

An additional aspect of a preferred embodiments may use zero-intermediate frequency architecture. In other embodiments, homodyne receivers are preferred. A processor module 304 may also be connected to an alarm system 306 (e.g., 911 emergency services, hospital notification system, etc.) or to any external network 307 whereby upon detecting events, signals may be sent or received to trigger alarms, notifications (i.e., email, text messaging, etc.), mechanical devices, electronic devices, or other mechanisms or actions by which event-detection precedes an action. In some embodiments, the event detected is an abnormality detected in an individual's gait.

Figure 5A:
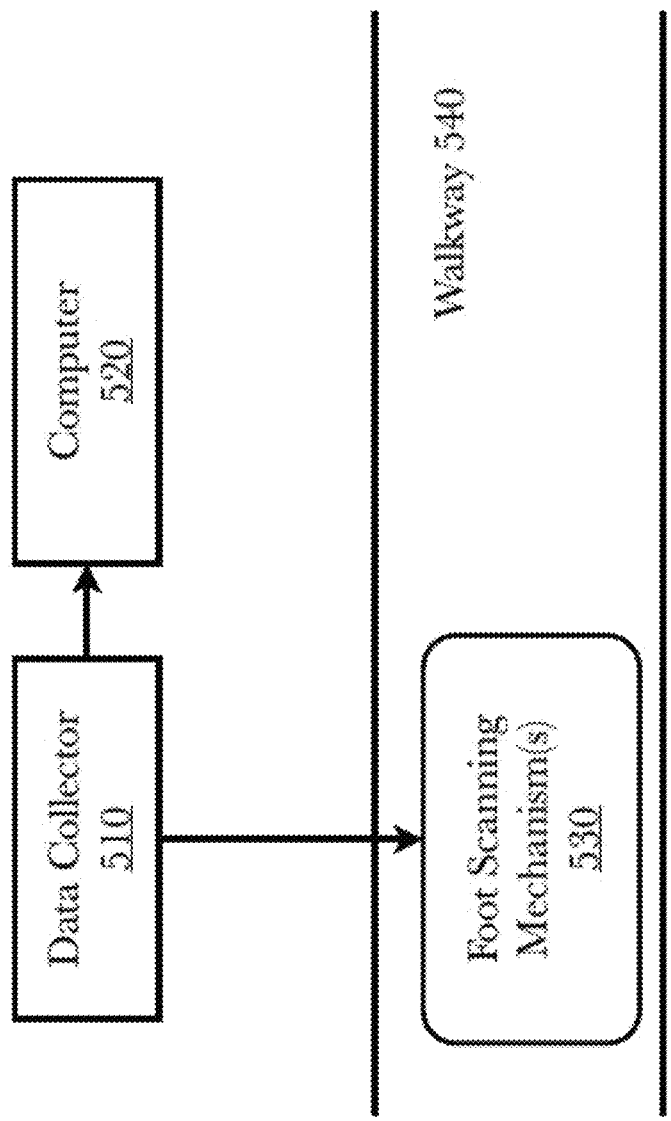
FIGS. 5A and 5B is a diagram illustrating a set-up for gathering and measuring gait data using floor sensors, according to an aspect.
Figure 5B:
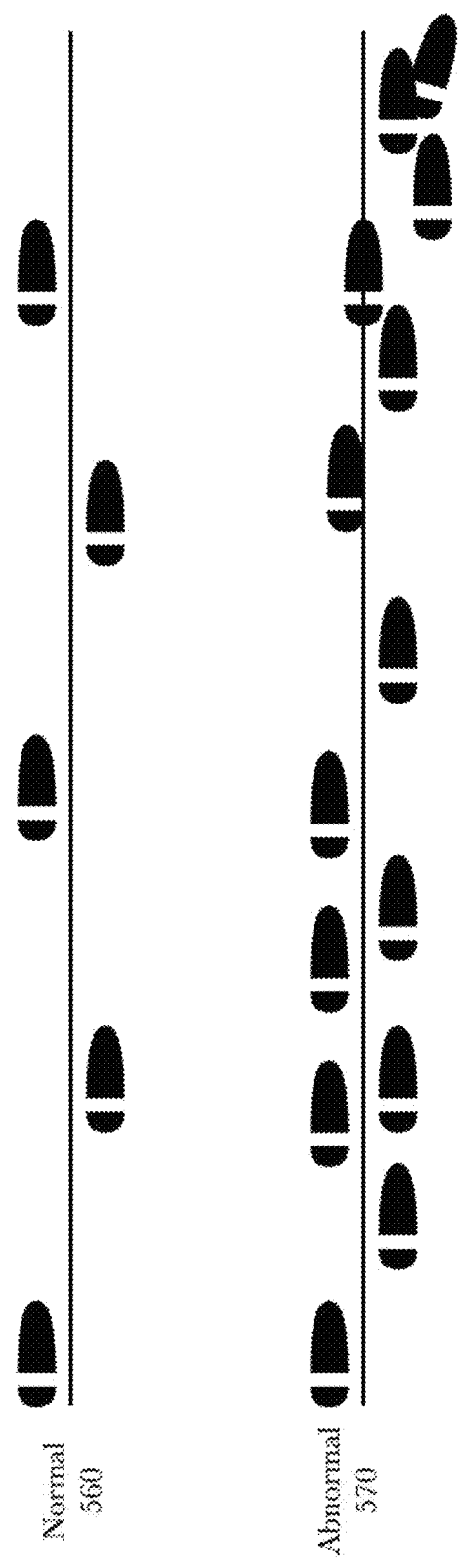

FIGS. 5A and 5B is a diagram illustrating a set-up for gathering and measuring gait data using floor sensors, according to an aspect. According to the aspect, a walkway 540 is prepared with one or more foot scanning mechanisms 530 which are configured to make measurements related to gait when a participant 550 walks across it, and send the measurements to data collector 510 which may or not be a separate component of a computing device 520 which process the received measurements to define the participant's gait and movement as either normal 560 or abnormal 570. In some embodiments, data collector 510 and/or computer 520 may be a specifically configured embodiment of a MCI-DAP platform 600 (referring to FIG. 6).

Data collection may be conducted in any suitable location such as a research laboratory (or other appropriate laboratories) equipped with walkway 540 and safety device (to prevent any accident). The system may extract gait patterns from recruited patients 550 (referring to FIG. 4) using IMDR system 100. System may also comprise a motion capture system 530 to capture gait signatures to compare with radar signature. According to various embodiments, two (or more) types of gait assessments can be conducted: single-task and dual-task walking of 10 meters. Single-task test: participants will be asked to walk on the walkway at their usual pace in a quiet, well-lit room wearing comfortable footwear without use of any mobility aids. Dual-task tests: participants will walk at their usual pace on the walkway while performing the following cognitive tasks aloud: (1) counting backward from 100 by ones, (2) subtracting serial sevens from 100, and (3) naming animals. They will walk toward the radar and across radar slowly and with/without arm swinging toward and away relative to the radar LOS, between approximately 4.5 m and 1 m from the antenna feed point. Each group will have at least 1,440 gait image patterns (=6 patients×3dual-tasks×2directions×2 arms-swing×20walks). These tests and the individual processes that make up these tests may change or vary as new data is gathered, inferred, and/or derived, or if the patient under study requires an augmented test due to a plurality of variables such as, for example, physical impairment.

Human gait features include velocity, number of steps per time unit (cadence), step length, stride length, step width, step angle, step time, swing time for each foot, support time, duration of the stops, existence of tremors when walking, angles of the different joints, body posture. MDSs of human gait have been investigated since the late 1990s by various researchers. The MDS pattern of normal 560 walking is a mono pattern (in 2D space) whereas abnormal 570 walking may sway and rock and, thus, appearing in a stereo 3D space which will only be captured by IMDR. The 3D MDSs are represented in a joint time-frequency domain that provides additional information in the time domain to exploit time-varying Doppler characteristics (spatiotemporal spectrogram) of the locomotion of human body and cadence-velocity diagram (CVD), where velocity is proportional to the observed Doppler shifts. System can extract physical feature and subspace feature sets on both STGF and CVD signature space. Physical features have been widely used for radar-based human activity recognition including: torso Doppler frequency, total Doppler bandwidth, offset of the total Doppler, Doppler bandwidth without micro-Doppler effects, period of the limb motion or stride rate, average radial velocity, stride length, radar cross-section of some moving body components (gait amplitude ratio), gait periodicity (corresponding to stride rate), maximal Doppler shift, etc. In subspace, system may apply principal component analysis for the intrinsic features of the walking styles bearing multiple correspondence to human motion kinematics using singular value decomposition to decompose the data matrix.

FIG. 6 is a block diagram illustrating an exemplary system architecture for a mild cognitive impairment—diagnostic and prognostic (MCI-DAP) platform 600 configured to process gait feature data using various algorithms to support early diagnosis and prognosis of MCI and AD, according to an embodiment.

According to various embodiments, a mild cognitive impairment—diagnostic and prognostic (MCI-DAP) platform 600 comprises: a machine learning engine 640 utilizing an incomplete multi-modality transfer learning algorithm (IMTL) extended with particle swarm optimization (IMTL-PSO) 641 and also utilizing one or more random forest classifiers 642 for classifying gait feature data; a deep learning engine 610 utilizing the IMTL integrated with a deep learning algorithm (IMTL-DL) 611; an IMDR processor 650; a patient model data store 630 which stores learned models and associated data, and an image processing engine 620 which prepares images 601 for machine and deep learning applications. The platform may be communicatively coupled to a clinician's terminal 670 and a records and imaging database(s) 680, whereby a clinician may request 604 to receive predictions 605 from the MCI-DAP platform 600 which retrieves patient data 604 from one or more records and imaging databases 680 and outputs a prediction 605. The records and imaging database 680 is also typically networked with radiology and other hospital departments such that a patient's image data is co-located with other medical information. Furthermore, the records and imaging database 680 as disclosed herein is merely exemplary and represents any digital or analog data store that holds image data and other medical data pertaining to patients.

According to the embodiment, MCI-DAP platform 600 may further comprise and IMDR system 100 which may be communicatively coupled to platform 600 for bi-directional communication. In one use case, a clinician may request 604 a diagnosis or prognosis of a patient about AD or MCI from platform 600 which can retrieve patient mobility data 602 (e.g., radar gait data, extracted gait features, etc.) either from records and imaging database 680, from some other storage system, or directly from IMDR system 603, and process the patient mobility data 602 using IMDR processor 650 according to the methods described herein. IMDR processor 650 may be configured to store patient models in patient model data store 630 as well as to output a predicted AD risk score 605 for a target patient. Because the IMDR processor manages and operates one or more machine and deep learning algorithms, in certain embodiments of platform 600 the random forest classifier 642 and LSTM network 612 may be trained, stored, and operated by machine learning engine 640 and deep learning engine 610, respectively.

In other embodiments, MCI-DAP platform 600 may receive a request for AD risk prediction for a target patient and may initiate IMDR system 603 as a service that receives target patient mobility data 602 and/or is able to capture patient mobility data (e.g., via IMDR antenna 110) and then processes the mobility data to output an AD risk score which can be sent, by MCI-DAP platform 600 to a clinician's terminal 670.

The machine learning engine 640 employing the incomplete multi-modality transfer learning algorithm (IMTL-PSO) 641 does not require filling in the modality-wise missing data. With an end goal to train an ML model for each patient sub-cohort, IMTL-PSO 641 couples the processes of training the sub-cohort-wise models together using an iterative EM algorithm to allow information transfer between the models. This is different from SM of each sub-cohort, with benefit of augmenting the sample size of each sub-cohort using the transferred information served as virtual samples, and thus producing estimators for the model coefficients with less variance—a nice statistical property leading to less variability (thus robustness) of using the model to make a diagnosis/prognosis.

According to the embodiment, machine learning engine 640 may also comprise an IMTL algorithm augmented with one or more various feature selection algorithms. According to some embodiments, the feature extraction algorithm is a particle swarm optimization (PSO) algorithm which is integrated with an IMTL algorithm to form the IMTL-PSO 641 algorithm.

The deep learning engine 610 is responsible for the training, deployment, and maintenance of deep learning models developed to make predictions on prognosis and diagnosis of mild cognitive impairment and Alzheimer's Disease for a given patient based on the patient's health record and any available imaging data. Deep learning engine 610 integrates one or more deep learning algorithms with IMTL forming an IMTL-DL algorithm 611. According to various embodiments, the deep learning algorithm may be a deep neural network. In some embodiments, the deep neural network may be a recurrent neural network, a convolutional neural network, various other types of deep learning algorithms, or some combination of deep learning algorithms. According to the embodiment, deep learning engine 610 may also perform various data processing tasks to train the deep learning algorithms therein. For example, deep learning engine 610 may receive a dataset, clean and transform it as necessary in order to be used as input into the one or more deep learning algorithms. Furthermore, deep learning engine 610 can be segregate a dataset or multiple datasets into a training dataset and a test dataset for algorithm training purposes.

According to some embodiments deep learning engine 610 may train one or more deep learning algorithms in a "training environment", wherein the one or more deep learning algorithms may be trained in a feedback loop. In the feedback loop, the algorithm is fed training input data, the output of the algorithm is compared against the expected output (contained in training dataset), and the comparison results is used as feedback to drive algorithmic updates such as, for example, parameter and hyperparameter optimization, and training dataset adjustments. A test dataset may be fed as input into a deep learning algorithm in the training environment, wherein the test dataset represents "new" data the algorithm has never processed before and the outputs based on the test dataset may be compared against the expected outputs. If the test was successful (e.g., criteria for success was met), then the deep learning algorithm has been fully trained into a model that can make accurate predictions. This trained model may be deployed to a "production environment" where it can begin receiving patient records and imaging data and make predictions on prognosis and diagnosis. The trained model may be sent to patient model data store 630 for storage and retrieval as needed. A clinician 670 may make a request 604 to platform 600 wherein the request contains patient mobility data 602, and the IMDR processor 650 can process the data to create a patient specific model that outputs patient specific predictions 605 which are received by the clinician at his or her terminal 670.

According to various embodiments, MCI-DAP platform 600 may be offered as a service to clinics and hospitals which provides a plurality of use cases including, but not limited to: computer aided diagnosis (CAD) to predict Alzheimer's Disease (AD), diagnosis of MCI due to AD, and prognosis of MCI due to AD; drug development, wherein the features used by the machine and deep learning algorithms may be used to identify potential attack vectors for potential drugs to treat MCI and/or AD; imaging acquisition augmentation; and a decision support system, wherein the predictions output by MCI-DAP platform 600 may be used a single data point for a patient or physician to use when seeking or providing medical care.

According to various embodiments, MCI-DAP platform 600 may be configured to make predictions about Alzheimer's Disease (AD) using non-imaging data. In some embodiments, non-imaging data may comprise movement and/or positional data of a patient as gathered by one various sensor systems (e.g., accelerometers, radar, LiDAR, gyroscopes, force sensors, pressure sensors, cameras, etc.) and fed into machine and deep learning algorithms to make predictions about AD progression.

Detailed Description of Exemplary Aspects

Figure 4:
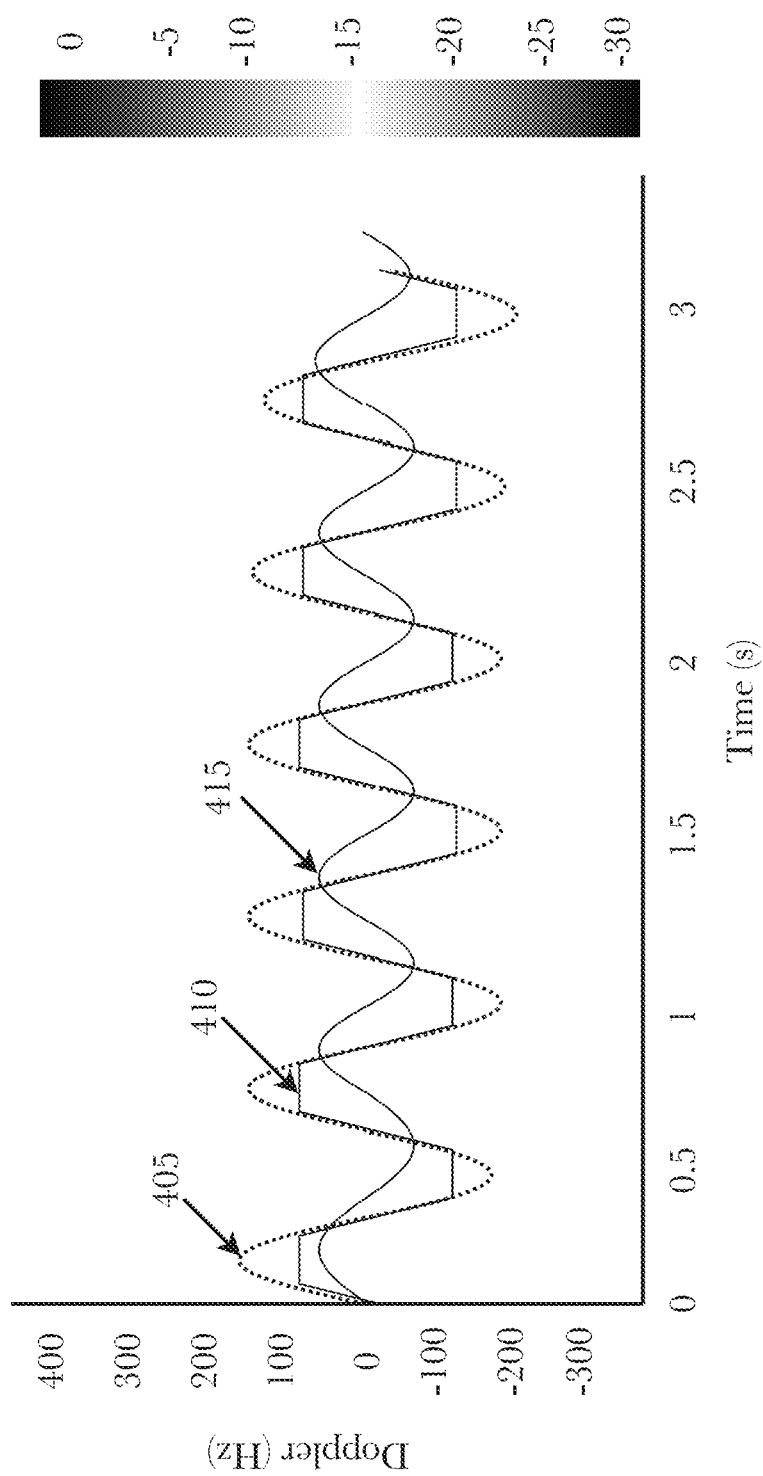
FIG. 4 is a diagram illustrating an exemplary micro-doppler signature (MDS) of a human walking in a time-frequency domain, according to an aspect.

FIG. 4 is a diagram illustrating an exemplary micro-doppler signature (MDS) of a human walking in a time-frequency domain, according to an aspect. The proposed IMDR system 100 can generate a STGF (or spatiotemporal spectrogram) represented in a joint time-frequency domain that provides information in the time (temporal) domain to exploit time-varying spatial velocity characteristics of the locomotion of human body segments such as, for example, the swinging arms and legs of a normal person walking. The STGF is a MDS in 3D. According to an embodiment, this exemplary MDS may be a typical output based on radar gait data collected by IMDR antenna 110. This exemplary MDS may be generated by arranging IMDR in such a way that it is pointing toward a participant as the participant is walking toward or across the radar. The participant may have his or her movement and position tracked by IMDR. Particularly, the movement of swinging arms and legs may be monitored and tracked in addition to the participants torso and head. The participant's movement and position may be determined and measured using 3-D coordinates (e.g., x-coordinate, y-coordinate, and z-coordinate) using the participants starting location as a point of origin, while also knowing the location of the IMDR system 100 relative to the origin.

As illustrated, the participant's locomotion may be monitored and described using a joint time-frequency domain plot wherein various signals may overlap and be accompanied by signal noise. Using various signal processing techniques and mechanisms, specific body parts and their associated signals may be identified from the overlapping signals. For example, the drawing shows a dotted sine wave which corresponds to the movement of participant's foot 405 during the time the participant was walking toward the radar. The semi-square wave 410 may correspond to another body part such as a clavicle or tibia, whereas the smaller sine 415 wave may correspond with the torso of the participant. Please note that these waveforms and corresponding body parts are simplified and used for illustrative purposes only.

During system training, all participants with AD may be able to walk for two (or more or less) minutes without using a walker (cane is acceptable). Participants may have a reasonable command of English language or use of English translator. Participants may be excluded if they have PD, drug-induced or vascular parkinsonism, any other coexisting neurological conditions or movement disorders, severe mental illness (major depression, bipolar disorder, schizophrenia), or evidence of stroke affecting motor function. According to embodiments, procedures established by the NINCDS-ADRDA Work Group and Dementia Rating Scale 2 (DRS-2) may also be administered in the recruitment process.

FIG. 7 is a flow diagram illustrating an exemplary method for a interferometric machine learning capable micro Doppler radar system, according to one aspect. The first step in the process is to acquire a gait signature 700 associated with an individual (e.g., clinical patient, etc.). This step leverages the interferometric micro-Doppler radar (IMDR) system 701 to capture a radar gait signature of an individual by transmitting one or more electromagnetic waves and receiving two or more reflected electromagnetic waves. The radar gait signature may comprise at least two signals related to the movement of the individual in a three-dimensional space. One of two signals is related to radial movement and the other of the two signals is related to transversal movement. Furthermore, a radar gait signal may be composed of one or more different views of the individual: a side view, a front view, a whole body view, a depth view, and a limb view. The signals received by IMDR may then be preprocessed 702 through an analog-to-digital converter (ADC) which transforms the radar gait signature into a digital representation which makes it the data easier to analyze and assess by other system components. The digitized version of the radar data may be used to create a spatiotemporal spectrogram 703 which represents the individuals locomotion (e.g., radial and transversal movement, various different views, etc.) and which can be used to perform gait signature analysis tasks at step 710. One or more machine and deep learning models are used to process the spectrogram in order to output a predicted risk score (i.e., individual classified as at risk of AD or not at risk of AD based on the individual's spectrogram. Regarding the one or more machine learning models, the spectrogram may first be fed through a feature extractor to extract features 712 from data contained within the spectrogram. The extracted features may then be used as input into a random forest classifier 713 which employs a plurality of decision trees on random sets of extracted features, wherein each of the plurality of decision trees outputs a prediction related to AD risk, and one or more rules are applied to the plurality of outputs to determine a unified and optimal prediction.

Regarding the one or more deep learning algorithms, the spectrogram data may be fed into a long short-term memory (LSTM) neural network at step 711 which is configured (i.e., trained) to make predictions related to AD risk for an individual based on the radar gait signature data as communicated through the spectrogram. Since the IMDR generates signatures from two perpendicular directions, in some embodiments two separate LSTM networks may be developed in parallel, wherein each LSTM is configured to process one of the two directions. Furthermore, cross-talk techniques can be employed to connect feature maps in the middle layers of the two LSTM networks to fully take advantage of the complementary information from the two networks and two directions.

The output from the one or more LSTM networks and random forest classifier may be integrated at step 714 using decision fusion techniques in order to generate the optimal classification results 720. In some embodiments, the decision fusion is a Bayesian classification problem that compares a likelihood ration with a minimum probability of classification error. An optimal decision fusion rule can be used with implementation of a modified back-propagation neural network training procedure. The determined optimal result 720 may be stored in a database associated with the individual (e.g., medical records database, patient model data store 630, etc.), it may be sent to a clinicians workstation if the output is a result of a clinician's request for an AD risk prediction, it may be used as a trigger to inform alert systems and/or other third party systems.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Referring now to FIG. 8, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 8 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

In some aspects, systems may be implemented on a standalone computing system. Referring now to FIG. 9, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 8). Examples of storage devices 26 include flash memory, magnetic hard drive, CD-ROM, and/or the like.

In some aspects, systems may be implemented on a distributed computing network, such as one having any number of clients and/or servers. Referring now to FIG. 10, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 9. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

FIG. 11 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A system for Alzheimer's disease risk quantification, comprising:
    a computing device comprising a memory, a processor, and a non-volatile data storage device; and a radio-frequency module comprising electronic components that cause the radio-frequency module to: transmit an electromagnetic wave; receive a reflected electromagnetic wave; convert the reflected electromagnetic wave into a digital signal; and send the digital signal to a processor module; and the processor module comprising a first plurality of programming instructions stored in the memory of, and operating on the processor of, the computing device, wherein the first plurality of programming instructions, when operating on the processor, cause the computing device to: receive the digital signal; process the digital signal into a spectrogram; and process the spectrogram through one or more deep learning algorithms for predicting an Alzheimer's disease risk score, wherein the system for Alzheimer's disease risk quantification use one or more interferometric radio frequency modules whereby a radar gait signature is received into a combined spectrogram processed by one or more deep learning algorithms for predicting the Alzheimer's disease risk score.

2. The system of claim 1, wherein the one or more deep learning algorithms is a long short-term memory neural network.

3. The system of claim 2, wherein two long short-term memory neural networks are developed in parallel.

4. The system of claim 3, wherein the two long short-term memory neural networks use cross-talk for connecting feature maps in the middle layers of each neural network.

5. The system of claim 1, wherein the radar gait signature comprises at least a radial movement and a transversal movement in three-dimensional space.

6. The system of claim 1, wherein the processor module is a software defined radio that can dynamically adapt to the available communication environment.

7. The system of claim 1, wherein the radar gait signature is generated from at least one of a side view, a front view, a depth view, a limbs view, and a whole body view.

8. The system of claim 1, wherein the processor module is further configured to:
    process the spectrogram through one or more machine learning algorithms for predicting a second Alzheimer's disease risk score; and
    integrate the Alzheimer's disease risk score and the second Alzheimer's disease risk score using decision fusion to determine an optimal risk score.

9. The system of claim 1, wherein the deep learning algorithms are trained on time-series data.

10. The system of claim 1, further comprising a graphical user interface whereby a user may interact with the interferometric radio frequency module or processor module inputs, settings, and outputs.

11. A method for Alzheimer's disease risk quantification, comprising:
    transmitting an electromagnetic wave;
    receiving a reflected electromagnetic wave;
    converting the reflected electromagnetic wave into a digital signal; and
    sending the digital signal to a processor module;
    receiving the digital signal;
    processing the digital signal into a spectrogram; and
    processing the spectrogram through one or more deep learning algorithms for predicting an Alzheimer's disease risk score, wherein the system for Alzheimer's disease risk quantification use one or more interferometric radio frequency modules whereby a radar gait signature is received into a combined spectrogram processed by one or more deep learning algorithms for predicting the Alzheimer's disease risk score.

12. The method of claim 11, wherein the one or more deep learning algorithms is a long short-term memory neural network.

13. The method of claim 12, wherein two long short-term memory neural networks are developed in parallel.

14. The method of claim 13, wherein the two long short-term memory neural networks use cross-talk for connecting feature maps in the middle layers of each neural network.

15. The method of claim 11, wherein the radar gait signature comprises at least a radial movement and a transversal movement in three-dimensional space.

16. The method of claim 11, wherein the processor module is a software defined radio that can dynamically adapt to the available communication environment.

17. The method of claim 11, wherein the radar gait signature is generated from at least one of a side view, a front view, a depth view, a limbs view, and a whole body view.

18. The method of claim 11, further comprising the steps of:
    processing the spectrogram through one or more machine learning algorithms for predicting a second Alzheimer's disease risk score; and
    integrating the Alzheimer's disease risk score and the second Alzheimer's disease risk score using decision fusion to determine an optimal risk score.

19. The method of claim 11, wherein the deep learning algorithms are trained on time-series data.

20. The method of claim 11, further comprising a graphical user interface whereby a user may interact with the interferometric radio frequency module or processor module inputs, settings, and outputs.

* * * * *